United States Patent
Wenske et al.

(10) Patent No.: US 10,010,452 B2
(45) Date of Patent: Jul. 3, 2018

(54) PRIMARY DRESSING FOR MOIST WOUND HEALING, AND METHOD FOR PRODUCING SAID PRIMARY DRESSING

(75) Inventors: Günther Wenske, Radeberg (DE); Gunter Boettcher, Würschnitz (DE)

(73) Assignee: KET Kunststoff-und Elasttechnik GmbH Liegau-Augustusbad, Radeberg (DE)

( * ) Notice: Subject to any disclaimer, the term of this patent is extended or adjusted under 35 U.S.C. 154(b) by 660 days.

(21) Appl. No.: 14/006,340

(22) PCT Filed: Mar. 21, 2012

(86) PCT No.: PCT/EP2012/054953
§ 371 (c)(1),
(2), (4) Date: Dec. 1, 2013

(87) PCT Pub. No.: WO2012/126929
PCT Pub. Date: Sep. 27, 2012

(65) Prior Publication Data
US 2014/0081192 A1    Mar. 20, 2014

(30) Foreign Application Priority Data

Mar. 21, 2011 (DE) .................. 10 2011 005 876
Jul. 8, 2011 (DE) .................. 10 2011 051 661

(51) Int. Cl.
*A61F 13/00* (2006.01)
*A61L 15/26* (2006.01)
(Continued)

(52) U.S. Cl.
CPC ........ *A61F 13/00038* (2013.01); *A61F 13/00* (2013.01); *A61F 13/00021* (2013.01);
(Continued)

(58) Field of Classification Search
CPC . A61F 2013/00119; A61F 2013/00225; A61L 2300/404
(Continued)

(56) References Cited

U.S. PATENT DOCUMENTS 4,034,751 A    7/1977  Hung
4,832,009 A *  5/1989  Dillon ............... A61F 13/0203
                                           424/447
(Continued)

FOREIGN PATENT DOCUMENTS

DE    44 07 031 A1    9/1995
EP    0 596 215 A1    5/1994
(Continued)

OTHER PUBLICATIONS

Integra Life Science Corporation: Integra Bilayer Wound Matrix—Treatment Guidelines—Collagen Soft Tissue Technology—company brochure dated 2010.

*Primary Examiner* — Kari Rodriquez
(74) *Attorney, Agent, or Firm* — Gudrun E. Huckett

(57) ABSTRACT

The invention relates to a primary dressing for moist wound healing with a reduced risk of inflammation. The elastic primary dressing according to the invention for moist wound healing is in the form of a lattice or a netting made of elongated elastic bodies, said lattice or netting containing non-resorbable elongated bodies that consist of silicone and optionally at least one additive selected from active pharmacological ingredients, collagens, hydrocolloids, and/or dyes. The lattice or netting preferably contains resorbable elongated bodies in addition to the non-resorbable elongated bodies, said resorbable elongated bodies containing at least one resorbable and bioactive organic compound, in particular selected from collagens and hydrocolloids. The invention also relates to a wound dressing that the primary dressing according to the invention contains in combination with a
(Continued)

secondary dressing. The invention also relates to methods for producing primary dressings according to the invention.

19 Claims, 3 Drawing Sheets

(51) Int. Cl.
    *A61L 15/32*     (2006.01)
    *A61L 15/42*     (2006.01)
    *A61L 15/44*     (2006.01)
    *B33Y 80/00*     (2015.01)

(52) U.S. Cl.
    CPC .............. *A61L 15/26* (2013.01); *A61L 15/325* (2013.01); *A61L 15/425* (2013.01); *A61L 15/44* (2013.01); *A61F 2013/00119* (2013.01); *A61F 2013/00225* (2013.01); *A61L 2300/404* (2013.01); *B33Y 80/00* (2014.12)

(58) Field of Classification Search
    USPC ................................................ 602/40–59, 76
    See application file for complete search history.

(56) References Cited

U.S. PATENT DOCUMENTS

| | | | |
|---|---|---|---|
| 4,921,704 A | 5/1990 | Fabo | |
| 2004/0133275 A1* | 7/2004 | Mansmann | A61F 2/30756 623/14.12 |
| 2008/0033333 A1* | 2/2008 | MacPhee | A61F 13/00012 602/50 |
| 2008/0138602 A1* | 6/2008 | Canham | A61B 17/06166 428/311.11 |
| 2010/0040759 A1* | 2/2010 | McLaughlin | A22C 7/00 426/644 |
| 2010/0280427 A1* | 11/2010 | Larsen | A61L 15/26 602/46 |
| 2011/0137223 A1* | 6/2011 | Daniel | A61L 15/12 602/76 |
| 2012/0089068 A1* | 4/2012 | McClure, Jr. | A61F 13/00029 602/48 |

FOREIGN PATENT DOCUMENTS

| | | |
|---|---|---|
| EP | 0 633 758 B1 | 1/1995 |
| GB | 2471021 A | 12/2010 |
| WO | 87/05206 | 9/1987 |
| WO | 2003/055534 | 7/2003 |

\* cited by examiner a)

b)

a)

b)

PRIMARY DRESSING FOR MOIST WOUND HEALING, AND METHOD FOR PRODUCING SAID PRIMARY DRESSING

BACKGROUND OF THE INVENTION

The invention concerns a primary dressing for moist wound care in the form of a lattice or netting containing elongate bodies of silicone and optionally active ingredients and/or dyes embedded therein, as well methods for its manufacture.

Chronic wounds that generate a lot of exudate and in which a granulation is to be promoted are treated according to the principle of moist wound care. In this context, a wound dressing is placed onto the wound that is suitable for absorbing wound secretion, prevents drying out of the wound surface, and maintains the physiological wound environment in this way. The healing process of the wound is coupled with vessel growth, fibroblast growth, and epithelial growth which grow in the wound for forming new tissue. When the wound during the healing process is covered with a fine-fiber wound dressing, there is, on the one hand, the risk of infections by growth of tissue into the fibers of the wound dressing. On the other hand, upon growth of tissue into the wound dressing, a non-traumatic removal of the wound dressing is not possible and the wound surface, upon removal of the wound dressing, is destroyed and the healing process is thereby prolonged.

For promoting granulation, in wound treatment open pore foam materials are used that adhere to the base of the wound. Hydrophilic foam materials ensure by increased capillary action a fast transport of the exudate to the exterior and ensure in this way a balanced moist wound environment. Due to the open pore structure, there is however the risk of ingrowth with the wound.

Functional wound dressings are constructed of three elements: primary dressing, secondary dressing and fixation. The primary dressing when in use is lying directly on the wound and is supposed to maintain a moist wound environment and transport away excess exudate from the wound. The primary dressing may not adhere to the wound so that a non-traumatic removal of the wound dressing is possible. The secondary dressing which is arranged on the side of the primary dressing which is facing away from the wound contains the absorptive body, for example, an open pore foam material that absorbs the wound exudate. Optionally, the secondary dressing comprises also a distribution layer which in use is positioned between primary dressing and absorptive body and which ensures a uniform distribution of the wound exudate. In order to prevent leaking through the dressing to the exterior, in the secondary dressing, on the side that is facing away from the wound, a liquid-impermeable but breathable protective layer is optionally arranged. In order to secure the position of the primary and secondary dressings during wound treatment, a bandage is applied. Suitable materials for the fixation are fixation bandages, tubular bandages, or adhesive fixation bandage The composition of the primary dressing which is lying directly on the wound is of enormous importance for the healing process. For preventing that the primary dressing will adhere to the surface of the wound, porous primary dressings with a hydrophobic silicone surface are proposed. Silicones are biocompatible and do not cause inflammation reactions. Due to their hydrophobic surface, cells cannot adhere, or only minimally adhere, to the surface of the silicone. They do not stick to the wound and enable in this way a non-traumatic removal. As a result of their excellent vapor permeability, silicones are particularly breathable. Through the pores, the wound exudate can be transported away well.

DE 4407031 A1 discloses a siliconized fiber nonwoven which is comprised of a support material of synthetic fibers, in particular polyester or polypropylene, and a silicone coating applied thereto at one or both sides. During manufacture, the support material is coated with a solvent-free addition-crosslinked silicon. In this way, on the fiber nonwoven a smooth surface is produced that advantageously should not stick to the wound surface.

WO 87/05206 discloses a primary dressing which comprises a stabilizing elastic netting with a hydrophobic gel layer, in particular a silicone gel layer or polyurethane gel layer. In this context, the netting is required on the one hand for stabilization and serves on the other hand for providing the pore system which is required for transporting the wound exudate through the primary dressing. Into the hydrophobic gel layer antibacterial active ingredients or substances that promote wound healing may be embedded. In order to avoid infections by fibers that become detached from the netting, it is required that the hydrophobic gel layer envelopes the netting completely (without any defects). Due to the hydrophobic gel layer, the fixation on the wound site is ensured, on the one hand; on the other hand, in particular because of the adhesion of the primary dressing due to the gel, there is the risk that the wound site will be damaged by removal of the primary dressing.

As a further development of WO 87/05206, EP 0633758 B1 discloses, as a protection against leaking, a wound bandage with a primary dressing of an elastic textile netting which, in analogy to WO 87/05206, is coated with and enveloped by a hydrophobic silicon gel layer. Furthermore, the wound dressing according to EP 0633758 B1 comprises an absorbent body (absorptive body) and a liquid barrier layer.

Wound dressings according to DE 4407031 A1, WO 87/05206, and EP 0633758 B1 have in common that they have a porous support structure that is provided with a silicon coating. In addition to the complex manufacture in two steps in which first the support structure to be coated is provided and, subsequently, is coated with silicone or a silicone gel, such wound dressings have the disadvantage that in case of defects of the enveloping structure detached fibers of the support structure may penetrate into the wound and may cause infections. By ingrowth of the tissue into the fibers of the support structure, a non-traumatic removal of the wound dressing is also at risk.

The invention has therefore the object to provide a primary dressing with a reduced inflammation risk and to provide methods for its manufacture.

SUMMARY OF THE INVENTION

The object is solved according to the invention by an elastic primary dressing for moist wound care in the form of a lattice or netting of elastic elongate bodies wherein the lattice or netting contains non-resorbable elongate bodies. The non-resorbable elongate bodies are comprised of silicone and optionally at least one additive selected from pharmacologically active ingredients, collagen, hydrocolloids and/or dyes. Preferred are non-resorbable elongate bodies that consist of silicone and optionally dyes.

In preferred embodiments of the invention, the lattice or netting contains, in addition to the non-resorbable elongate bodies, also resorbable elongate bodies which contain at least one resorbable and bioactive organic compound, in particular selected from collagen and hydrocolloids.

The primary dressing according to the invention does not represent an open pore structure that is coated with silicone but the material of individual strands of the lattice structure or netting structure itself is silicone which optionally contains active ingredients and/or dyes which either are contained in the silicone matrix or are present as components of a resorbable coating on the surface of the lattice or netting.

Optionally, in the lattice structure or netting structure further strands of resorbable materials are contained that upon use in wound care are decomposed and thereby preferably release bioactive substances and/or active ingredients.

Silicone is biologically not decomposed (i.e., it is thus not resorbable) and is very inert. Allergic reactions for surface-type applications are not known for silicone. Since with the primary dressing according to the invention no coated support structure is present, the primary dressing according to the invention advantageously does not cause any inflammation reactions against further components of the primary dressing.

A primary dressing according to the invention is present in the form of a flat lattice or netting. Non-resorbable elastic elongate bodies of silicone, in which may be embedded optionally pharmacologically active substances, collagen, hydrocolloids and/or dyes, are linked therein to an open pore structure. Due to the open pore configuration of the primary dressing, it is ensured that the exudate can be effectively transported away. By use of the inert and biocompatible silicone, a painless and damage-free removal of the wound dressing is possible.

In addition to the non-traumatic removal, the active promotion of wound healing is one aspect of preferred embodiments of the primary dressing. This is effected in that bioactive substances and/or pharmacologically active ingredients are introduced into the primary dressing. They are present preferably embedded as a component of the non-resorbable elongate bodies in the silicone and/or are part of a resorbable coating on the surface of the lattice or netting and/or, in addition to the non-resorbable elongate bodies in the primary dressing, further resorbable elongate bodies are contained which contain resorbable and bioactive organic compounds. In this way, it is possible to introduce into the primary dressing bioactive substances or active ingredients that are released in use on the wound. In any case, the primary dressing is designed such that, even after resorption of the resorbable elongate bodies, a non-resorbable web with a lattice structure or netting structure remains.

Resorbable materials in the meaning of the invention differ from non-resorbable materials in that, in use on the wound, they are metabolized, for example, by cells that are present in the wound, and are decomposed in this way over time. Non-resorbable materials are not metabolized and remain permanently present. Bioactive substances in the meaning of the invention are substances that actively promote wound healing. Preferred bioactive substances are collagens. They are natural components of the skin and accelerate the healing process by new growth of skin. The primary dressing according to the invention ensures as a result of its open pore flexible structure an ideal wound environment and, in addition thereto, collagen promotes the healing process.

Further preferred resorbable materials are hydrocolloids (in particular alginates). It is preferred that they are in the form of a hydrogel.

Coatings that are present on the primary dressings according to the invention are exclusively resorbable. No non-resorbable coatings are present on the primary dressings according to the invention (in particular, no coatings that contain silicones). When applying resorbable coatings, the primary dressing is preferably left on the wound surface until the coating has been decomposed and a non-traumatic removal of the primary dressing is possible.

Primary dressings according to the invention are obtainable by methods of three-dimensional printing (3D printing), screen printing or textile processing methods, in particular weaving, warp knitting, or weft knitting. As a function of the respective manufacturing process, the lattice structure or netting structure of the primary dressing is differently fixed. When the primary dressing is a lattice that is produced by 3D printing or screen printing, the elongate bodies interpenetrate at their crossing points in the lattice so that in this way a fixation as a result of interpenetration is ensured. When the primary dressing is a lattice or netting produced by a textile processing method, the individual strands do not interpenetrate at their crossing points. The fixation of the lattice structure or netting structure of the primary dressing is in this case ensured by an adhesive edge that is applied to the edge of the primary dressing. Basically, any medically approved adhesive is suitable for this purpose (e.g. hot melts). Preferred materials for the adhesive edge are adhesive silicones because they bond well with the silicone of the lattice structure or netting structure.

The three-dimensional structure of the primary dressing according to the invention is an open pore structure and, as a result of its manufacture, is a lattice or netting. Primary dressings in the form of a lattice can be obtained by 3D printing, screen printing or weaving. Primary dressings in the form of a netting can be obtained by warp knitting or weft knitting. The structure of the primary dressing is an open pore structure so that it is possible to transport away the wound exudate.

When the primary dressing is present in the form of a lattice, the latter comprises at least two crossed layers of parallel elongate bodies (strands). Preferred primary dressings are comprised of two crossed layers of parallel strands. For the use on deep wounds, primary dressings with more than two layers of parallel strands are preferred.

The primary dressing according to the invention is elastic and contains non-resorbable elongate bodies which are not metabolized. This enables on the one hand an adaptation to the wound surface and a permanent protection from adhesion to the wound.

Silicones that are contained in the primary dressings according to the invention as non-resorbable components are preferably crosslinked silicones, in particular elastic silicone rubbers. Silicone rubbers contain as base polymers polyorganosiloxanes which contain functional groups, in particular H atoms, OH groups and vinyl groups that are accessible for crosslinking reactions.

Preferred are room temperature vulcanizing silicone rubbers (RTV), high temperature vulcanizing silicone rubbers (HTV, LSR/liquid silicone rubber), and UV-crosslinking silicones. Single component RTV silicone rubbers polymerize under the action of moisture in the air wherein crosslinking is realized by condensation of SiOH groups with formation of Si, O bonds. Two-component RTV silicone rubbers contain as a further component a crosslinking agent, in particular mixtures of silicic acid esters or organic tin compounds. Upon crosslinking, the formation of an Si—O—Si bridge from ≡Si—OR and ≡Si—OH by alcohol cleavage occurs. HTV silicone rubbers are plastically deformable flowable silicones that contain highly dispersed silicic acid and crosslinking catalysts, in particular organic peroxides or platinum compounds. HTV silicone rubbers vulcanize generally by treatment at temperatures above 100° C.

The silicone surface in a primary dressing according to the invention has preferably a hydrophobic surface that has the advantage that cells cannot grow, or only minimally grow, on the surface. Still, primary dressings with a hydrophobic surface adhere well to the wound site without sticking. By surface modification, on the primary dressing according to the invention a hydrophilic surface can be generated. This promotes the wound exudate being transport away faster.

Preferred are primary dressings according to the invention with a hydrophobic surface because the latter favors, as a result of the reduced cell adherence, a non-traumatic removal of the primary dressing.

Preferably, the elongate bodies of the primary dressing have a round or oval cross-section area. In this way, advantageously the contact surface of the primary dressing on the wound is minimized. This contributes also to a simpler removal of the primary dressing from the wound without mechanical destruction of the newly formed tissue. Accordingly, the primary dressing according to the invention in the form of a lattice or a netting with round or oval elongate bodies has a hydrophilic or hydrophobic surface.

Depending on the exudate quantity of the wound, improved carry-off can be achieved by means of different pore sizes. In the meaning of the invention, pore size of the primary dressing refers to the spacing of two elongate bodies that are positioned next to each other (measured relative to the exterior side of the elongate body). A primary dressing according to the invention has preferably a pore size of 0.5-1.2 mm. Preferred is a pore size of 0.8-1 mm.

The vertical extension of the elongate bodies of the primary dressing (in case that they have a round cross-section area, the diameter of the cross-sectional surface of the elongate body) is preferably 0.5-1 mm, especially preferred 0.6-0.8 mm.

The vertical extension of the entire primary dressing (thickness) which comprises at least two layers of elongate bodies is preferably maximally 4 mm, preferably maximally 2 millimeter, particularly preferred maximally 1.5 mm, especially preferred between 0.7 and 1.5 mm.

Preferably, the primary dressing according to the invention is produced in the size that is predetermined for its use, preferably with a surface area of maximally 1,600 cm$^2$, more preferred maximally 400 cm$^2$ (wherein the shape of the primary dressing can be any shape, for example, rectangular, square, round, ellipsoid, or the like). Stamping or cutting of the primary dressings which leads to a laterally open and sharp-edged border of the primary dressing (resulting more likely in colonizing of microorganisms in comparison to closed rims) is avoided in this way. When the primary dressing is produced in the application size, the lateral border of the primary dressing is preferably free of cut edges. The lateral border has preferably a closed and rounded structure (non-traumatic border structure).

Further preferred, on the lateral border of the primary dressing according to the invention a pull tab of non-resorbable elongate bodies is applied. The non-resorbable elongate bodies form in this context the tab arranged laterally on the lattice or the netting. In the position of use, the pull tab is not positioned immediately on the wound. Removal of the primary dressing from the wound is facilitated in this way because the primary dressing, by pulling on the pull tab, can be removed in an uncomplicated and non-traumatic way.

For actively promoting wound healing, a primary dressing according to the invention preferably contains pharmacologically active ingredients, preferably antibacterial active ingredients or active ingredients that promote wound healing. They are contained in the silicone, are present in a coating on the surface of the lattice structure or netting structure, and/or are embedded in the resorbable elongate bodies of the lattice structure.

Preferably, the resorbable elongate bodies contain an antibacterial active ingredient, preferably an antiseptic wound treatment agent, particularly preferred an antiseptic wound treatment agent that is active against bacteria and fungi. A particularly preferred antiseptic wound treatment agent is polihexanide.

The antibacterial active ingredient is preferably contained in an antiseptically active concentration in the resorbable elongate bodies. Suitable concentrations of polihexanide are 0.01 to 0.1% by volume.

Preferably, no dyes are contained in the primary dressing according to the invention. In this way, the wound surface when using transparent silicones is already visible without removal of the primary dressing. Optionally, the medically approved and harmless dyes can be embedded in the silicone.

The invention comprises also a wound dressing for moist wound care that comprises a primary dressing according to the invention and a secondary dressing with a porous absorptive body. In use, the primary dressing is lying immediately on the wound, the secondary dressing is located on the side of the wound dressing which in use is facing away from the wound surface. Preferably, the porous absorptive body has a hydrophilic surface. Preferred porous absorptive bodies are foams of polyurethane or silicone. The raw density of the foam is preferably 100 to 250 kg/m$^3$, in particular 120 to 180 kg/m$^3$ with a preferred cell number per running centimeter: 10+/−4 (pores per centimeter). The compression strength (i.e., the physical pressure in Pascal acting on a surface in square meters that is required to compress the foam by 40%) of the porous absorptive body is preferably 3-15 kPa, particularly preferred 4 to 8 kPa. The tensile strength of the porous absorptive body is preferably at least 100 kPa (determined according to DIN 53571 A). The elongation at break of the porous absorptive body is preferably at least 60% (determined according to DIN 53571 A). Preferably, the porous absorptive body has a vertical extension (thickness) of 5 to 25 mm.

The secondary dressing comprises in addition to the porous absorptive body preferably a liquid barrier layer and/or an odor-binding layer.

The wound dressing according to the invention contains in addition to the primary and secondary dressing preferably a fixation means. The fixation means is preferably selected from fixation bandages, tubular bandages or adhesive fixation bandages. In this way, it is ensured that the position of the wound dressing remains unchanged during wound treatment.

Primary dressings according to the invention can be manufactured by various methods. Methods for producing primary dressings according to the invention by 3D printing, screen printing and weaving, warp knitting or weft knitting are also subject matter of the invention. The primary dressing according to the invention is preferably produced by methods of 3D printing in that a fast curing viscous material is shaped layer by layer by extruding. In this method, the data saved on a computer are directly converted for producing a three-dimensional body.

In the method according to the invention for a layer-by-layer production of a primary dressing with a lattice structure of at least two layers of elongate bodies that cross each other by means of 3D printing, a first layer of parallel arranged elongate bodies is applied for providing the lattice structure and, subsequently, onto the first layer a second layer of elongate bodies arranged parallel to each other is applied wherein the elongate bodies of the first layer and the elongate bodies of the second layer have an angle relative to each other of 1 to 90° so that the elongate bodies of the first and the second layers are crossing each other.

The application of the elongate bodies is realized by extrusion of a viscous material wherein the material is comprised of crosslinking silicone and optionally pharmacologically active substances and/or dyes. By crosslinking of the silicone an elastic solid material is obtained. Methods of extrusion are known from the prior art. It is preferred that the extrusion is done through a nozzle with a maximum extension (for a round cross-section: maximum diameter) of 0.5 to 1 mm (herein also referred to as "microextrusion").

The manufacture of the primary dressing by means of 3D printing is done layer by layer wherein first a first layer of elongate bodies is applied parallel to each other and, subsequently, onto the first layer a second layer of elongate bodies that are parallel to each other is applied. Optionally, in this way further layers of elongate bodies are applied. In this context, the elongate bodies of different layers are displaced relative to each other at an angle of 1 to 90° so that the elongate bodies of the stacked layers cross each other. At least two layers of elongate bodies are applied by the method according to the invention. Preferred is that precisely two layers of elongate bodies are applied so that a lattice structure with two layers of crossing elongate bodies is obtained. The elongate bodies which are applied in the method according to the invention for providing the lattice structure are preferably provided with a round or oval cross-section area.

Pharmacologically active ingredients, preferably antibacterial active ingredients and/or active ingredients that promote wound healing are optionally contained in the viscous material that is processed by extrusion (in particular microextrusion) in the aforementioned manufacturing process. Moreover, optionally dyes, in particular mineral pigment preparations containing pigments in combination with a silicon oil, are contained in the viscous material.

The method for producing a primary dressing according to the invention by means of 3D printing provides the possibility of incorporating, in addition to the non-resorbable strands of silicone (and optionally active ingredients and/or dyes), also resorbable strands into the lattice structure. For this purpose, in the same way as described for the elongate bodies of silicone and optionally active ingredients and/or dyes, elongate bodies are formed of a viscous material and incorporated into the lattice. The viscous material for providing the resorbable strands contains in this context exclusively resorbable materials, in particular at least one resorbable and bioactive organic compound, particularly preferred selected from collagen, hydrocolloids and pharmacologically active substances. Particularly preferred is collagen.

In the method according to the invention for producing a primary dressing with a lattice structure by means of screen printing, the lattice structure is generated by screen printing of a viscous material of crosslinking silicone and optionally pharmacologically active ingredients and/or dyes. In this context, a lattice of optionally several layers is generated wherein after each applied layer crosslinking of the silicone is carried out.

For the methods for producing a primary dressing by means of 3D printing or screen printing, the viscous material, comprised of silicone optionally with pharmacologically active substances and/or dyes, and/or the viscous material for providing the resorbable strands preferably have a viscosity of 300,000 mPas to 1,000,000 mPas at a shear rate of 10 s$^{-1}$ (determined in a rotary viscometer).

For producing a primary dressing according to the invention by means of 3D printing or screen printing, crosslinking elastic silicone rubbers, in particular LSR and RTV silicone rubber, liquid silicone, HTV silicone rubber, or UV crosslinking silicone are preferred.

Depending on the type of employed silicone, crosslinking of the silicone is realized by different reactions. Single component RTV silicone rubbers crosslink by moisture in the air without further method steps being required. Two-component RTV silicone rubbers are mixed before processing the viscous material in the methods according to the invention (3D printing or screen printing) so that crosslinking is started. After manufacture of the primary dressing no further method steps are thus required in order to effect curing of the viscous material. Primary dressings on the basis of HTV silicone rubber are crosslinked after processing of the viscous material to the lattice structure by temperature treatment at temperatures above 100° C. Primary dressings on the basis of UV crosslinking silicone are exposed to UV radiation after providing the lattice structure so that the silicone will crosslink.

The invention comprises also a method for producing an elastic primary dressing for moist wound care in the form of a lattice or netting in which the lattice or netting is produced by textile processing, in particular by weaving, warp knitting, stitching, weft knitting, from elongate bodies, wherein the elastic elongate bodies are comprised of silicone and optionally pharmacologically active ingredients and/or dyes. The elongate bodies, preferably elastic strands of silicone and optionally pharmacologically active substances and/or dyes with a thickness of maximally 1.5 mm, preferably maximally 1 mm, have preferably a round or oval cross-ssection area. Preferably, resorbable elongate bodies (as defined above) are incorporated additionally into the lattice or netting.

With the aforementioned methods according to the invention, preferably primary dressings in application size (no web material or large sheets) are produced. Preferably, by the methods according to the invention, primary dressings are generated whose surface area does not surpass 1,600 cm$^2$, preferably 400 cm$^2$. Preferably, in a method according to the invention, the primary dressing is not further treated by a cutting process (for example, stamping or cutting) after providing the lattice or netting. This has the result that primary dressings are produced that have a border structure that is free of sharp edges and preferably is rounded.

For producing such a border structure, extrusion methods, in particular the aforementioned 3D printing, are preferred. In this connection, the lattice structure is generated in which the elongate bodies that are arranged parallel to each other are comprised of an interconnected individual strand which is arranged in a meander shape (see FIGS. 3a, 3c). This has the advantage that sharp-edged borders at the primary dressing are avoided and in this way a better biocompatibility of the primary dressing is achieved.

Preferably, in one of the methods according to the invention, a pull tab of non-resorbable elongate bodies is generated at the lateral end of the lattice or netting. The pull tab is elongate and enables advantageously an easier removal of the primary dressing. Preferably, such a pull tab (see for example FIGS. 3b, 3d) is produced by extrusion methods, in particular by methods of 3D printing.

In case that by an inventive method resorbable strands are incorporated into the lattice or netting, the resorbable elongate bodies preferably contain an antibacterial active ingredient, preferably an antiseptic wound treatment agent. Particularly preferred are antiseptic wound treatment agents that are active against bacteria as well as fungi. A particularly preferred antibacterial active agent is polihexanide.

After providing the primary dressing by the aforementioned methods and optionally crosslinking of the silicone, an elastic primary dressing for moist wound care is obtainable that has a hydrophobic surface.

In a further method step, the surface of the primary dressing obtainable by the method according to the invention is optionally converted into a hydrophilic surface. This is realized preferably by plasma treatment, flame treatment or by wet-chemical treatment in a solution with MSA copolymers, preferably by plasma treatment or flame treatment.

Subsequent to a hydrophilic treatment, onto the surface of the lattice or netting preferably a resorbable coating is applied which contains a pharmacologically active ingredient and/or at least one resorbable organic compound, in particular selected from collagen and hydrocolloids. Preferred are active ingredient-containing and/or collagen-containing coatings. In use of the primary dressing on the wound, this coating is decomposed and the active ingredients and/or bioactive components are released.

Methods of 3D printing, extrusion and screen printing are known as such in the prior art. The solution according to the invention however provides the possibility of using these methods also in connection with moist wound care. Therefore, the invention comprises also the use of methods of 3D printing, extrusion, and screen printing, in particular of methods of 3D printing, for producing primary dressings for moist wound care. Particularly preferred is the use of 3D printing, extrusion, and screen printing of elastic silicone rubbers for producing primary dressings for moist wound care.

Elongate bodies, in particular fibers, of silicone are known from the prior art. With the invention, they are now advantageously used in moist wound care. Therefore, the invention comprises also the use of elongate bodies, in particular fibers, of silicone and optionally pharmacologically active ingredients and/or dyes for producing primary dressings for moist wound care. Particularly preferred in this context is the use in one of the methods according to the invention, in particular weaving, warp knitting, stitching, or weft knitting.

Lattices or nettings produced by 3D printing, screen printing, or textile-processing methods are known from the prior art. In the invention, lattices or nettings with elongate bodies of silicone, which contain optionally active ingredients and dyes, are used for moist wound care. Therefore, the invention comprises also the use of a lattice or netting which comprises non-resorbable elongate bodies of silicone and optionally at least one additive selected from pharmacologically active ingredients, collagen, hydrocolloids and/or dyes, and wherein the lattice or netting is obtainable by 3D printing, screen printing, warp knitting, weaving, stitching or weft knitting, for moist wound care, in particular as a primary dressing for moist wound care.

Medical indications in which the solution according to the invention is used comprise all wounds with exudate formation, in particular ulcerations in the phase of granulation. Particularly preferred medical indications are chronic lower leg ulcers, split-skin graft removal sites, and burns.

The invention provides methods with which a primary dressing of silicone can be produced in a reproducible way with a defined pore system. The primary dressing obtained in this way for moist wound care contains non-resorbable elongate bodies of silicone and optionally active ingredients and/or dyes. A two-stage coating of supporting netting structures of plastic material with silicone gels is not required in the method according to the invention. A risk of inflammations by defect sites in the silicone layer and of incompatibility of the body with components of the support structure is therefore advantageously not present.

In other respects, the primary dressings according to the invention have the same advantages as known wound dressings with silicon coating. Due to the porous open pore structure the drainage of wound exudate is ensured. The silicone surface enables as a result of the minimal cell adherence a non-traumatic removal of the wound dressing. By use of round or oval strands in the lattice structure or netting structure, the contact surface area can be advantageously reduced which further facilitates removal of the primary dressing.

The primary dressings according to the invention have the advantage that they can be selected individually depending on the specific conditions of the respective patient, and a suitable pore size and/or suitable strand cross-section can be selected. An effective exudate drainage as a result of the open pore structure is possible. As a result of the capillary action a fast transport of wound exudate is ensured and, still, a moist wound environment is maintained. As a result of the surface tension of the silicone, the primary dressings adhere to the wound and do not necessarily require further adhesives for fixation.

BRIEF DESCRIPTION OF THE DRAWINGS

With the aid of the following figures and embodiments, the invention will be explained in more detail without limiting the invention thereto.

DESCRIPTION OF PREFERRED EMBODIMENTS

Embodiment 1: Primary Dressing of Two Layers According to the Invention

Figure 1:
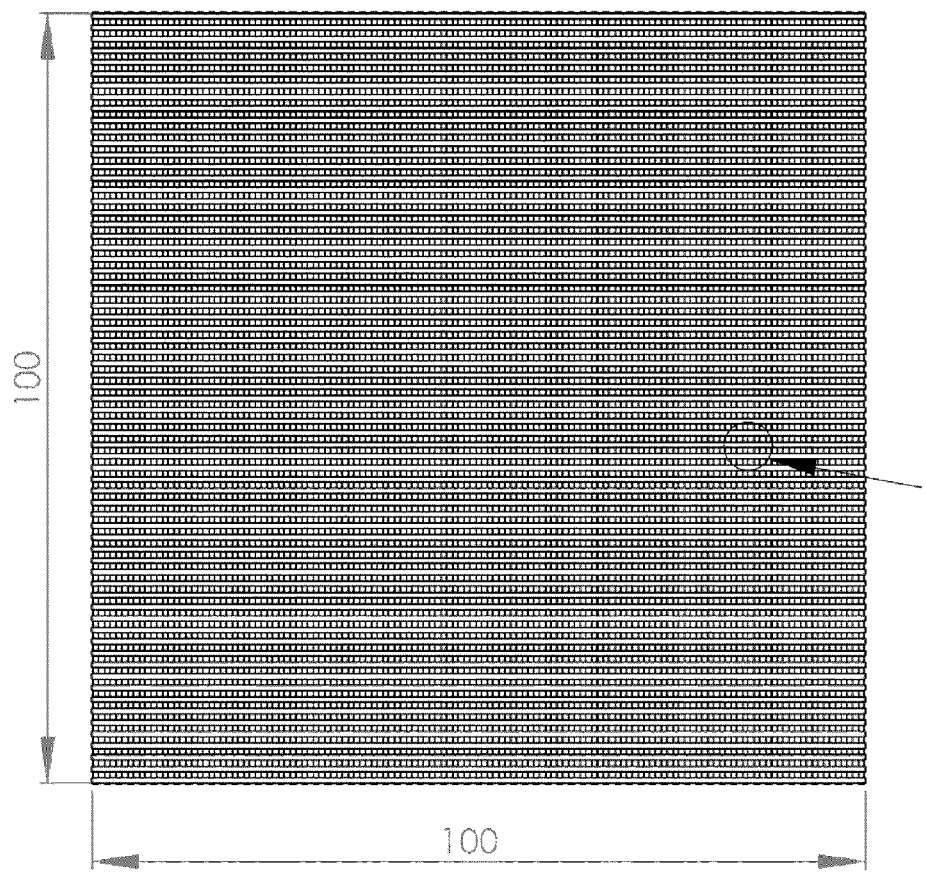
FIG. 1 Primary dressing according to the invention of two layers of elongate bodies with round cross-section area (plan view), values in [[mm]]. a) shows the plan view of the complete primary dressing, b) shows an enlargement of the detail indicated in a).
Figure 1:
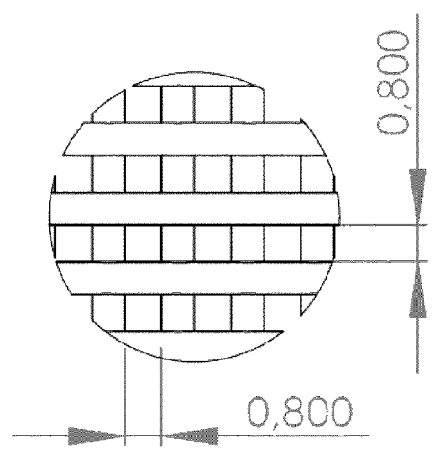
Figure 2:
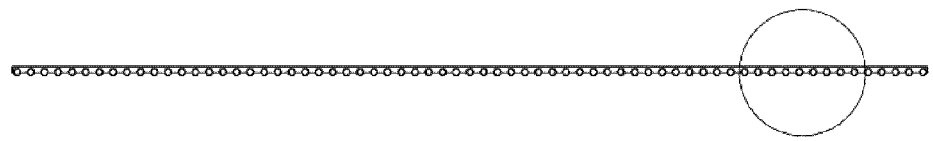
FIG. 2 Primary dressing according to the invention of two layers of elongate bodies with round cross-section area (side view), values in [[mm]]. a) shows the side view of the complete primary dressing, b) shows a enlargement of the detail indicated in a).
Figure 2:
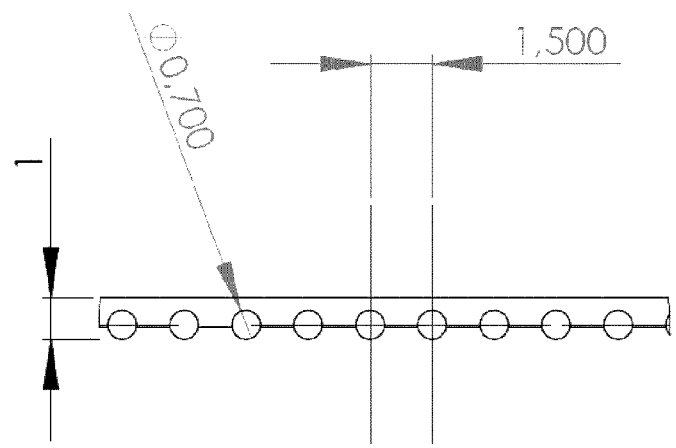

FIGS. 1 and 2 show a plan view and a side view, respectively, of the primary dressing according to the invention of two layers of round bodies arranged parallel to each other and produced by 3D printing of liquid silicone. The diameter of the cross-section area of the elongate bodies is 0.7 mm (FIG. 2b). The bodies are arranged at a spacing of 0.8 mm (FIG. 1b, corresponds to 1.5 mm spacing of the center points of the elongate bodies, FIG. 2b). The vertical extension of the primary dressing according to the invention is 1 mm (FIG. 2b). The primary dressing is provided in a square shape with a lateral length of 100 mm (FIG. 1a).

Embodiment 2: Use of a Primary Dressing According to the Invention

The primary dressing according to the invention of embodiment 1 was applied onto a wound surface such that the primary dressing projected past the edge of the wound by at least 1 cm. On top of the primary dressing according to the invention a polyurethane foam of the same size was arranged which fulfills the function of a porous absorptive body. Onto the polyurethane foam, sterile ES compresses were applied and the wound dressing was secured by a gauze bandage.

It was observed that the wound dressing with the primary dressing according to the invention prevents the wound from drying out and promotes wound healing. The formed tissue did not grow into the primary dressing. It was possible to remove the wound dressing without mechanical destruction of the formed tissue. Inflammation reactions and allergic reactions caused by the primary dressing were not observed.

Figure 3:
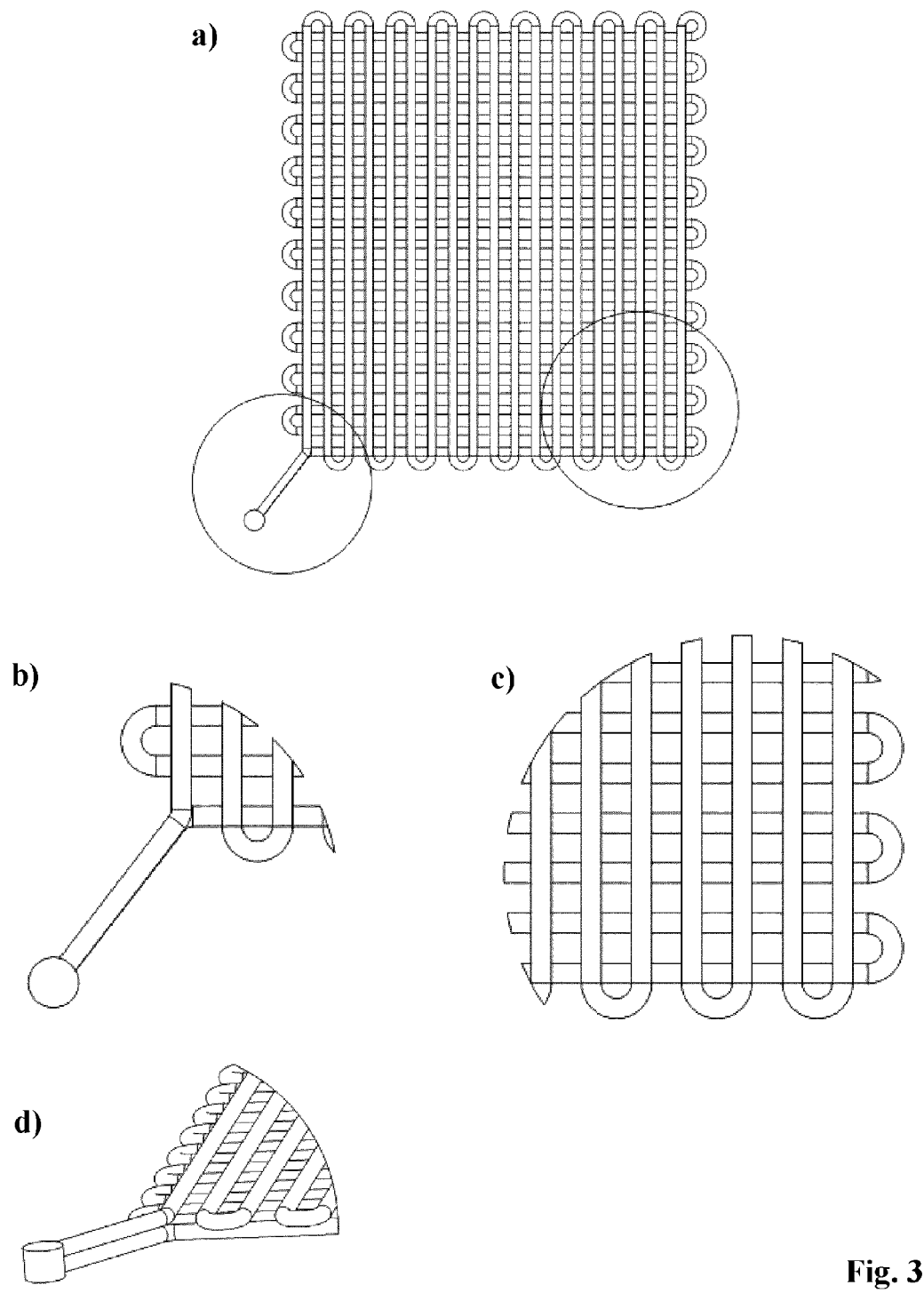
FIG. 3 Primary dressing according to the invention of two layers of elongate bodies with border structure that is free of cut edges and has a pull tab. a) shows the plan view of the complete primary dressing, b) shows an enlargement of the detail indicated at the lower left in a), c) shows an enlargement of the detail indicated at the lower right in a), d) shows a pull tab that has been produced by 3D printing.

Embodiment 3: Two-Layer Primary Dressing with Border Structure without Cut Edge and with Pull Tab FIG. 3 shows a primary dressing in lattice structure of two layers of parallel elongate bodies. The primary dressing is obtained by extrusion by means of 3D printing. For this purpose, the lattice structure is applied by means of a single strand of a viscous silicone material. For building the pull tab, first a partial strand is generated that forms the lower part of the pull tab (see FIG. 3D). In order to produce the lattice structure, a first layer of meandering elongate bodies arranged parallel to each other is generated and, subsequently, a further layer is applied onto the first layer from the same individual strand. After completion of the second layer, the end of the individual strand is deposited onto the surface or immediately adjacent to the partial strand. It forms the pull tab (FIGS. 3b and d) which in use is not lying directly on the wound so that it will not stick to the wound. Removal of the wound dressing is facilitated in this way. Due to the meandering arrangement of the parallel elongate bodies, a rounded border structure is produced. No cutting to size of the primary dressing is required so that the border structure remains free of cut edges.

What is claimed is:

1. An elastic primary wound dressing for moist wound care, wherein the elastic primary wound dressing is a flat lattice or netting structure, wherein the flat lattice or netting structure consists of a lattice or netting consisting of a first layer and a second layer of non-resorbable elongate bodies, wherein the non-resorbable elongate bodies consist of silicone and of at least one additive that is selected from the group consisting of pharmacologically active ingredients, collagen, hydrocolloids, and dyes, wherein the elastic primary wound dressing is configured to be placed directly onto a wound, wherein the first layer is comprised of a first meandering strand arranged in a meandering arrangement forming a first set of the elongate bodies, arranged parallel to each other and joined by U-shaped bends, wherein the second layer is comprised of a second meandering strand arranged in a meandering arrangement forming a second set of the elongate bodies, arranged parallel to each other and joined by U-shaped bends, wherein the first set of the elongate bodies and the second set of the elongate bodies cross each other, wherein the U-shaped bends provide a lateral border about a periphery of the elastic primary wound dressing that provides a closed and rounded, non-traumatic structure.

2. The primary dressing according to claim 1, wherein the silicone is crosslinked silicone selected from the group consisting of liquid silicone, RTV (room temperature vulcanizing) silicone rubber, HTV (high temperature vulcanizing) silicone rubber, and UV (ultraviolet) crosslinkable silicone.

3. The primary dressing according to claim 1, wherein the pharmacologically active ingredients are antibacterial active ingredients and/or active ingredients for promoting wound healing and are embedded in the silicone of the non-resorbable elongate bodies.

4. The primary dressing according to claim 1, wherein the lateral border is free of cut edges.

5. The primary dressing according to claim 1, wherein the non-resorbable elongate bodies are 3D-printed to cross each other at crossing points and form the first and second layers, wherein the non-resorbable elongate bodies at the crossing points interpenetrate each other.

6. The primary dressing according to claim 1, wherein the non-resorbable elongate bodies of the lattice or netting have a thickness of maximally 1.5 mm.

7. The primary dressing according to claim 1, wherein the first meandering strand and the second meandering strand have an end extending past the lateral border to provide a pull tab.

8. A method for producing an elastic primary dressing according to claim 1 for moist wound care in the form of a lattice or netting, the method comprising the steps of:
  employing elastic non-resorbable elongate bodies consisting of silicone and of at least one additive that is selected from the group consisting of pharmacologically active ingredients, collagen, hydrocolloids, and dyes;
  building the lattice or netting from the elastic non-resorbable elongate bodies by weaving, warp knitting, stitching, or weft knitting.

9. The method according to claim 8, comprising producing the primary dressing in an application size of a surface area of maximally 1,600 $cm^2$.

10. The method according to claim 8, comprising producing on a lateral end of the lattice or netting a pull tab.

11. An elastic primary wound dressing for moist wound care, wherein the elastic primary wound dressing is a flat lattice or netting structure, wherein the flat lattice or netting structure consists of a lattice or netting consisting of a first layer and a second layer of non-resorbable elongate bodies, wherein the non-resorbable elongate bodies consist of silicone, wherein the elastic primary wound dressing is configured to be placed directly onto a wound, wherein the first layer is comprised of a first meandering strand arranged in a meandering arrangement forming a first set of the elongate bodies, arranged parallel to each other and joined by U-shaped bends, wherein the second layer is comprised of a second meandering strand arranged in a meandering arrangement forming a second set of the elongate bodies, arranged parallel to each other and joined by U-shaped bends, wherein the first set of the elongate bodies and the second set of the elongate bodies cross each other, wherein the U-shaped bends provide a lateral border about a periphery of the elastic primary wound dressing that provides a closed and rounded, non-traumatic structure.

12. The primary dressing according to claim 11, wherein the silicone is crosslinked silicone selected from the group consisting of liquid silicone, RTV (room temperature vulcanizing) silicone rubber, HTV (high temperature vulcanizing) silicone rubber, and UV (ultraviolet) crosslinkable silicone.

13. The primary dressing according to claim 11, wherein the lateral border is free of cut edges.

14. The primary dressing according to claim 11, wherein the non-resorbable elongate bodies are 3D-printed to cross each other at crossing points and form the first and second layers, wherein the non-resorbable elongate bodies at the crossing points interpenetrate each other.

15. The primary dressing according to claim 11, wherein the non-resorbable elongate bodies of the lattice or netting have a thickness of maximally 1.5 mm.

16. The primary dressing according to claim 11, wherein the first meandering strand and the second meandering strand have an end extending past the lateral border to provide a pull tab.

17. A method for producing an elastic primary dressing according to claim 11 for moist wound care in the form of a lattice or netting, the method comprising the steps of:

employing elastic non-resorbable elongate bodies consisting of silicone, building the lattice or netting from the elastic non-resorbable elongate bodies by weaving, warp knitting, stitching, or weft knitting.

18. The method according to claim 17, comprising producing the primary dressing in an application size of a surface area of maximally 1,600 cm$^2$.

19. The method according to claim 17, comprising producing on a lateral end of the lattice or netting a pull tab.

* * * * *